United States Patent
Suovaniemi et al.

(10) Patent No.: US 8,758,812 B2
(45) Date of Patent: Jun. 24, 2014

(54) COMPOSITION FOR FOODSTUFF FOR BINDING ACETALDEHYDE

(75) Inventors: Osmo Suovaniemi, Helsinki (FI); Ville Salaspuro, Helsinki (FI); Martti Marvola, Helsinki (FI); Mikko Salaspuro, Helsinki (FI)

(73) Assignee: Biohit Oyj, Helsinki (FI)

( * ) Notice: Subject to any disclaimer, the term of this patent is extended or adjusted under 35 U.S.C. 154(b) by 718 days.

(21) Appl. No.: 12/301,925

(22) PCT Filed: May 22, 2007

(86) PCT No.: PCT/FI2007/050288
§ 371 (c)(1),
(2), (4) Date: Jan. 27, 2009

(87) PCT Pub. No.: WO2007/135242
PCT Pub. Date: Nov. 29, 2007

(65) Prior Publication Data
US 2010/0239663 A1    Sep. 23, 2010

Related U.S. Application Data

(60) Provisional application No. 60/802,120, filed on May 22, 2006.

(30) Foreign Application Priority Data

May 22, 2006  (FI) ..................... 20060501

(51) Int. Cl.
*A61K 9/22*    (2006.01)

(52) U.S. Cl.
USPC ........................................ 424/457

(58) Field of Classification Search
None
See application file for complete search history.

(56) References Cited

U.S. PATENT DOCUMENTS

2005/0271754 A1    12/2005    Cochrane

FOREIGN PATENT DOCUMENTS

| JP | 4-21635 A | 1/1992 |
| WO | 02/36098 A1 | 5/2002 |
| WO | WO 0236098 A1 * | 5/2002 |
| WO | 2006/103316 A1 | 10/2006 |
| WO | WO 2006103316 A1 * | 10/2006 |

OTHER PUBLICATIONS

V. Salaspuro, et al, "Binding of Ethanol Derived Carcinogenic Acetaldehyde in Colonic Contents by Slow-Releasing L-Cysteine Tablet", Alcoholism Clinical and Experimental Research, May 2002, 139A, vol. 26, 5 Supplement, S.
Ville Salaspuro, et al, "Removal of Acetaldehyde From Saliva by a Slow-Release Buccal Tablet of L-Cysteine", International Journal of Cancer, 2002, pp. 361-364, Vol. 97, XP002908015.
Ville J. Salaspuro, et al, "Eliminating Carcinogenic Acetaldehyde by Cysteine From Saliva During Smoking" Cancer Epidemiol Biomarkers Prev, Jan. 2006, pp. 146-149, vol. 15, No. 1, XP002449219.

* cited by examiner

*Primary Examiner* — Anand Desai
*Assistant Examiner* — Melissa Mercier
(74) *Attorney, Agent, or Firm* — Sughrue Mion, PLLC

(57) ABSTRACT

This invention relates to a non-toxic composition which bind acetaldehyde present in the stomach, intestine and/or colon. The composition comprises one or more acetaldehyde-binding compound(s) comprising one or more free sulphhydryl and/or amino groups. The compound(s) are mixed with a non-toxic carrier that effects sustained release of said compound(s) in the gastrointestinal tract. This invention relates also to food additives and food compositions and packages comprising the composition.

31 Claims, No Drawings

COMPOSITION FOR FOODSTUFF FOR BINDING ACETALDEHYDE

CROSS REFERENCE TO RELATED APPLICATION

This application is a National Stage of International Application No. PCT/FI2007/050288 filed May 22, 2007, which claims priority based on Finish Patent Application No. 20060501, filed May 22, 2006, and which claims the benefit of U.S. Patent Publication No. 60/802,120 filed May 22, 2006, the contents of all of which are incorporated herein by reference in their entirety.

This invention relates to a composition according to the preamble of claim 1 to reduce or remove the acetaldehyde contained in the stomach or in the stomach, intestine and/or colon. This invention relates also to food additives, food compositions, food packages and uses according to the preamble of claims 31, 32, 33 and 37.

Both alcohol and smoking are risk factors for upper digestive tract cancers, and the combined use thereof multiplies the risk of developing an upper digestive tract cancer to as much as 150-fold (Salaspuro, M. Best Pract Res Clin. Gastroenterol (2003) 17:679-94 and Francheschi et al. Cancer Res (1990) 50:6502-07).

The first metabolite of alcohol is acetaldehyde. It has been shown to be carcinogenic both to test animals and humans (Salaspuro, M. Crit Rev Clin Lab Sci (2003) 40: 183-208). Alcohol is evenly distributed in the liquid phase of the organs. Hence, after enjoying alcohol and as long as there is alcohol in the organs, the alcohol content in blood, saliva, gastric juice and the contents of the intestine is the same. In that case, the microbes in the digestive tract are capable of oxidizing the alcohol to acetaldehyde. For example, even after a moderate dose of ethanol (0.5 g/kg), high acetaldehyde contents of a microbial origin (18-143 µM) have been found in human saliva; in other words, acetaldehyde builds up in saliva as an intermediate product of the microbial metabolism (Homann et al, Carcinogenesis (1997) 18:1739-1743). During active smoking, the acetaldehyde in saliva was increased to a value of 261.4±45.5 µM from the basic level (Salaspuro et al. (2004) Int J Cancer, 2004 Sep. 10; 111(4):480-3).

Asian heavy drinkers, who have a familial low-activity modification of the aldehyde dehydrogenase-2 (ALDH2) enzyme, have both an increased risk of developing a cancer of the mouth, the pharynx and the digestive tract, and an increased acetaldehyde content of the saliva after consuming alcohol (Väkeväinen et al. (2000) Alcohol Clin Exp Res 24:873-877). Even more common is the ADH3*1 gene/allele (ADH1C at present), which predisposes the heavy drinkers, who have this gene, to the upper digestive tract cancers because of increased local acetaldehyde contents. (Visapää J-P et al. Gut. 2004 June; 53(6):871-6.)

In the organism, acetaldehyde is thus formed from alcohol as a consequence of the hepatic metabolism and, locally, in the digestive tract via microbial alcohol dehydrogenase (Salaspuro et al, (1996) Ann Med 28:195-200). The average amount of saliva secreted by a human is 1.5 liters per day. The areas of influence of the acetaldehyde contained in the saliva include the mouth, the pharynx, the oesophagus and the stomach. Consequently, the effects of acetaldehyde may extend to the whole upper digestive tract area. On the other hand, carcinogenic acetaldehyde can be produced also endogenously by the oral microbes from various foodstuffs with high sugar or carbohydrate content, especially in an achlorhydric stomach. Atrophic gastritis and achlorhydria are well known risk factors of gastric cancer.

As a consequence of the microbial metabolism, acetaldehyde builds up in the stomach in the case, where the stomach is free from acid or has been made acid-free by medication Väkeväinen et al. (2000) Alimentary Pharmacology Ther 14:1511-1518) describes an experiment, where the pH of stomach fluid was raised from pH 1.3 to 6.1. Volunteers were given ethanol (0.6 g/kg as 15 vol % solution). After 40 minutes incubation there were in the gastric juice 0.7 to 4.1% alcohol and 30 µM to 100 µM acetaldehyde. The acetaldehyde content of the gastric juice was the higher the more there were bacteria in the stomach. In the gastric juice there were for example *Streptococcus viridans*-bacteria, which have been shown to be excellent producers of acetaldehyde. Other effective acetaldehyde producers in acid-free stomach have been shown to be bacteria belonging to *Neisseria, Rothia* and *Streptococcus salivarius* (Väkeväinen (2002) et al. Scand J Gastroenterol 37:648-655).

For atrophic gastritis patients, microbes produce high acetaldehyde contents from ethanol and sugar in the stomach leading to an enhanced gastric cancer risk among atrophic gastritis patients (Väkeväinen et al, Scand J Gastroenterol 2002 (6): 648-655). In the experiments of Väkeväinen et al. sugar (3 ml/kg, 10 w-% glucose) or ethanol (0.3 g/kg; 15 vol-%) were infused to stomach. After sugar infusion and 60 minutes incubation three patients from 16 had 2.3 to 13.3 µM endogenous acetaldehyde and 2.3 to 13.3 µM ethanol in their stomach. After alcohol infusion the average amount of acetaldehyde was 44.5 µM which is 6.5 times more than what controls had.

Our recent studies show that in an achlorhydric stomach alcohol fermentation can start very quickly by the bacteria representing normal flora of the mouth or by yeasts present in the foodstuffs, for example by common baker's or brewer's yeast. These microbes can produce significant amounts of acetaldehyde and ethanol for example from carbohydrate containing foodstuffs, such as rice. This happens in particular, if the carbohydrate containing foodstuff is sweetened. For example in Asian countries the use of sweet sauces with rice is a very common practise. According to epidemiological studies the eating of rice causes a high risk for cancer in stomach.

In acid stomach the alcohol fermentation does not occur. On the other hand *Helicobacter pylori* infection and certain medicaments, such as Protein Pump Inhibitors (PPI) raise the pH of the stomach.

About nearly 25% of the human population in the world suffers from atrophic gastritis. From the Finnish population about 8 to 12% (depending on the age) suffers from atrophic gastritis and the disease is even more common among elder people. The development of achlorhydric stomach is a risk factor also for people having oesophagus reflux disease, if it is treated by PPI medicamends. About 25% of the human population in the world has this disease.

One further risk factor are foodstuffs comprising acetaldehyde. Our recent studies have shown that all sugar (saccharose, maltose, lactose) containing foodstuffs including beverages, can contain—or in the foodstuff is formed—significant amounts of acetaldehyde, 5 to 2000 µM and ethanol, 0.1 to 0.5 per mille. Some sour milks, yoghurts and juices contain acetaldehyde and ethanol as such (PCT/FI2006/000104 incorporated herein by reference).

It has also been shown that acetaldehyde builds up in the large intestine, as its bacteria that represent the normal flora are capable of converting ethanol into acetaldehyde (Jokelainen et al, (1996) Gut 39:100-104). In the intestines, endogenous ethanol can also be found, i.e. ethanol that is formed in the intestines in oxygen-free conditions under the effect of microbes. Acetaldehyde is formed, when this ethanol comes into contact with oxygen near the mucous membrane, for example.

The prior art discloses pharmaceutical compositions which contain compounds that bind acetaldehyde, their effect being based on the reaction of the effective substances with the acetaldehyde inside blood and/or cells, for example, U.S. Pat. No. 5,202,354, U.S. Pat. No. 4,496,548, U.S. Pat. No. 4,528,295, U.S. Pat. No. 5,922,346.

Acetaldehyde, which is formed in the organism when alcohol is consumed and thereafter, causes physiological symptoms called a hangover. Previously, efforts have been made to decrease the symptoms caused by acetaldehyde by taking preparations containing ascorbic acid, thiamine, cysteine or cysteic acid, and flavonoids or flavonoid complexes in a form of orally taken tablets in connection with, before or after consuming alcohol. When swallowed, the effective substances go to the stomach and small intestine and from there into the blood circulation (Matsuoka, U.S. Pat. No. 5,202,354 and Moldowan et al, U.S. Pat. No. 4,496,548).

Publication WO 02/36098 (incorporated herein by reference) suggests the use of compounds containing a free sulphhydryl and/or amino group for a local and long-term binding of acetaldehyde from saliva, the stomach or the large intestine. The compounds were mixed with a substance that enabled them to be released for at least 30 minutes in the conditions of the mouth, the stomach or the large intestine.

Publication WO 2006/037848 (incorporated herein by reference) suggest a composition comprising one or more free sulphhydryl and/or amino groups for removing or decreasing the aldehyde content of the saliva during smoking.

As on the basis of our recent studies, acetaldehyde plays a considerable part in the pathogenesis of the stomach cancers, in particular by people having achlorhydric stomach or atrophic gastritis. There is thus a need to find alternative ways to bind acetaldehyde in the stomach and also lower part of digestive tract in a harmless manner. There is also a need to develop new compositions capable of binding acetaldehyde and methods of administration of such compositions.

SUMMARY

It is an aim of the present invention to provide new compositions, which can be used to reduce the acetaldehyde content in the stomach.

It is also an aim of the present invention to provide new compositions, which can be consumed to reduce the acetaldehyde content of small intestine (called here intestine) and/or large intestine (called here colon).

It is also an aim of the present invention to provide new compositions, which mask the taste of the acetaldehyde-binding compound)(s) in the composition. In particular, it is an aim of the invention to provide new compositions, in which the acetaldehyde-binding compound(s) are protected not to be released too early, i.e. in mouth when they are consumed or if they are mixed with a foodstuff, in the foodstuff.

It is also an aim of this invention to provide new food additives, food compositions or food packages, which comprise compositions, which can be used to reduce the acetaldehyde content in the stomach, intestine and/or colon.

These and other objects, together with the advantages thereof over known compositions and methods are achieved by the present invention, as hereinafter described and claimed.

One object of the present invention is thus a composition, which comprises one or more acetaldehyde-binding compounds.

According to the invention the composition binds acetaldehyde present in the stomach or in the stomach, intestine and/or colon, and comprises one or more acetaldehyde-binding compound(s), which are bound to a non-toxic carrier that effects, in the stomach, sustained release of said compound(s) into the stomach.

To be more precise, the composition according to the invention is characterized in that, what is stated in the characterizing part of claim 1.

According to one preferred embodiment of the invention, the compositions of the invention are packed or bottled to a package aimed at consumers, the content of which is suitable to be added to the foodstuff before eating. The foodstuffs may be liquid, solid or semi-solid foodstuffs. It is advantageous to add the compositions of the invention to products that remain in the stomach for a longer period of time. The composition of the invention can be added to a foodstuff also as mixed to another foodstuff. It is also of advantage, if the compositions are mixed with a foodstuff just before eating. The composition may be packed in a separate package and the package comprising the acetaldehyde-binding compounds is added to another package comprising a food composition just before eating.

According to another preferred embodiment of the invention the compositions of the invention are protected not to be released too early, in mouth, or if the compositions is mixed with a foodstuff, in the foodstuff, but released in the stomach. The compositions may be covered or coated by a water-soluble film. This hinders effectively the potentially unpleasant taste of acetaldehyde-binding compound(s). The compositions may be protected also by a tablet or capsule, preferably a hard gelatine or HPMC capsule or other form of preparation.

The composition of the invention binds the acetaldehyde contained in the foodstuffs, and/or which is produced by microbes from alcohol or from sugar and carbohydrates in non-acid stomach or from any other source.

The invention provides considerable advantages. The compositions comprising acetaldehyde-binding compounds can be used to reduce the risk of developing the cancer of the stomach, the intestine and/or colon of people having increased risk for cancer in these areas. The compositions of the invention are in particular suitable for people suffering from atrophic gastritis, achlorhydric and low acid stomach. More specifically, by the compositions of the present invention are suitable for people having atrophic gastritis, atrophic gastritis of corpus or atrophic gastritis of antrum or achlorhydric or low acid stomach or *Helicobacter pylori* infection. In particular, the compositions according to the invention can be used for decreasing the risk of cancer or for treating people having at least one of the biomarkers of atrophic gastritis. Such biomarkers are low pepsinogen I (PI) level, low pepsinogen I (PI)/pepsinogen II (PII) ratio, high gastrin-17 level compared to the reference range or cut-off values. Furthermore, the compositions according to the invention can be used for decreasing the risk of cancer or for treating people having at least one of the biomarkers of achlorhydric or low acid stomach. Such biomarkers are high gastrin-17 value, high PI value and high PII value compared to the reference range values. High HPAB (*Helicobacter pylori* antibody) value is a biomarker of atrophic gastritis and achlorhydric and low acid stomach, since it may raise the pH of the stomach. All these biomarkers can be tested by commercially available GastroPanel®.

Furthermore, the compositions of the present invention are particularly effective for binding acetaldehyde, when they are consumed in connection of eating, before, during or after eating. The composition is capable of releasing acetaldehyde-binding compounds in stomach during the time the foodstuff is digested. However, the compositions can be used also in a continuous manner, for example after every 8 to 10 hours. The composition may comprise a carrier that does not dissolve in the stomach or comprises a water insoluble film releasing the effective substance only slowly. Alternatively the composition may comprise substances which form a gel in the stomach or which adhere the composition to the mucous membrane of the stomach.

Consuming the compositions according to the invention mainly binds acetaldehyde locally, but it may also have a systemic effect.

In addition, the compositions according to the invention can be used for large-scale consumers of alcohol, or those who have hangover, smokers and those, who have a familial low-activity modification of the aldehyde dehydrogenase-2 (ALDH2) enzyme or the ADH3*1 gene/allele (ADH1C*1 at present). The use of the compositions according to the invention is also of benefit to those who consume moderate amounts of alcohol or who consume foodstuffs that contain small contents of alcohol or acetaldehyde.

DETAILED DESCRIPTION OF THE INVENTION

Definitions

A composition comprising acetaldehyde-binding compound(s) means in connection of this invention a composition which comprises a non-toxic carrier(s), which is/are not harmful for human (or animal) consumption. The composition may mean a functional food additive comprising a liquid or solid material intended to be added to a foodstuff or it may mean a product for reducing the risks for diseases. The composition may also mean a pharmaceutical composition comprising pharmaceutically acceptable carriers. The compositions are in particular suitable for oral administration. The carriers as such may comprise the same substances and it depends on the legislation of the country, whether the composition should be called a food additive, a product for reducing the risks for diseases or a pharmaceutical composition. The aim of the composition is to decrease the risk for cancer in the gastro-intestinal tract.

The composition comprises an effective amount of acetaldehyde-binding compound(s). An effective amount means an amount capable of binding or inactivating the amount of acetaldehyde present in a foodstuff or formed during the digesting of a foodstuff in the stomach after eating. An effective amount may mean also an amount capable of binding or inactivating the amount of acetaldehyde present in the stomach due to acetaldehyde formed from alcohol or for other reasons in stomach and/or in intestine and/or colon.

"A composition for binding acetaldehyde present in the stomach" means here a composition, which comprises one or more acetaldehyde-binding compound(s). Preferably said compound(s) comprise one or more free sulphhydryl and/or amino groups, more preferably one or more free sulphhydryl and/or amino groups. Instead of sulphhydryl group may be used sulphone group.

The composition comprises a non-toxic carrier that effects, in the stomach, sustained release of said compound(s) in the stomach. Sustained or prolonged release means the release of effective substances for at least 30 minutes in the conditions of the stomach. Preferably the effective substances release for 0.5 to 8 hours, preferably 2 to 6 hours, most preferably 2 to 4 hours or 1 to 4 hours.

According to a preferred embodiment of the invention the compositions are taken in connection of eating, preferably during the eating, before the eating or after eating. The composition can be for example mixed to the foodstuff or it can be taken before or after eating. Advantageously, the compositions are mixed with a foodstuff or food composition just before eating. The composition preferably releases the effective compound(s) the time the foodstuff is in the stomach i.e. during the digestion of the food. This time is typically 2 to 4 hours. Food compositions and foodstuffs, into which the acetaldehyde binding compositions of the present invention can be added are disclosed for example in PCT/FI2006/000104 incorporated herein by reference.

According to some embodiments of the invention the dosage may be renewed by 4 to 10 hour intervals, preferably at 6 to 8-hour intervals.

The amount of acetaldehyde-binding compound(s) that is added to a foodstuff depends on the amounts of these foodstuffs the consumer is most likely to enjoy at one time. The amount of added substances also depends on, whether the foodstuff in question already contains acetaldehyde-binding compounds, such as cysteine. The amount of substances to be added also depends on, whether the foodstuff already contains acetaldehyde. For example, 1 to 5000 mg/kg, preferably 5 to 4000 mg/kg, more preferably 5 to 3000 mg/kg, even more preferably 5 to 2000 mg/kg, still more preferably 5 to 1000 mg/kg, even more preferably 5 to 500 mg/kg, even more preferably 5 to 300 mg/kg, most preferably 5 to 100 mg of acetaldehyde-binding compound per kilo of food composition can be added to the product.

A single dose of acetaldehyde binding compound is preferably 20-200 mg, typically 50-100 mg.

According to preferred embodiment of the invention, the compositions of the invention are packed or bottled to a package aimed at consumers, the content of which is suitable to be added to the foodstuff before eating. The foodstuffs may be liquid, solid or semi-solid foodstuffs. Particularly suitable foodstuffs are milk products. It is advantageous to add the compositions of the invention to products that remain in the stomach for a longer period of time, such as sour milk, soured whole milk, and yoghurt. The composition of the invention can be added to a foodstuff also as mixed to another foodstuff. Compositions comprising acetaldehyde binding compounds can be mixed for example to grain products, such as cereals, muesli, flour, chips, snacks and crackers.

The composition according to the invention may be in the form of a preparation, for example a tablet, a capsule, a granule, powder, or a tablet or a capsule comprising powder or granules. The composition may be in a form of a monolithic or multiparticular preparation, such as tablet or capsule or granule.

A single dose of the preparation may be a tablet or capsule or suitable amount of granules or a tablet or capsule comprising granules or powder.

It is of advantage if the composition is in the form of a preparation, the diameter of which is at least 7 mm, preferably 8 to 15 mm, more preferably 11 to 15 mm. This assists the preparation to stay in the stomach sufficient time for the sustained release of acetaldehyde-binding compound(s).

The amount of compound(s) released in the conditions of the stomach is preferably 40-80 mg in an hour.

The task of the carrier in the composition is sustained release of the effective compound(s) in the conditions of the stomach.

According to one preferred embodiment of the invention the composition comprises a carrier that does not dissolve or dissolves only poorly in the stomach. Alternatively the composition may be covered by a water insoluble film.

According to another embodiment of the invention the carrier may form a gel in the stomach that floats in the contents of the stomach.

According to one further embodiment of the invention the preparation may be a liquid preparation taken orally (mixture), the physical structure of which is a gel.

According to one further embodiment of the invention the preparation may attach to the mucous membrane of the stomach.

According to one preferred embodiment of the invention the composition comprises a carrier that does not dissolve in the stomach. Such a carrier may be a polymer, such as metacrylate polymer, for example poly(ethyl acrylate-co-methyl methacrylate-co-trimethylammonioethyl methacrylate chloride 1:2:0.1) (EUDRAGIT RS) or poly(methacrylic acid-co-methyl methacrylate 1:2) (EUDRAGIT S), or ethyl cellulose.

The composition may comprise substances selected from the group comprising one or more acetaldehyde-binding compound(s), a polymer not dissolving in the stomach and a bulking agent.

The composition preferably comprises acetaldehyde-binding compound(s) 1 to 40 w-%, preferably 5 to 40, more preferably 10 to 30 w-%. Typically the amount is 20 to 25 w-%.

The composition preferably comprises polymers 10-50 w-% preferably 20 to 40 w-%, more preferably 20 to 30 w-%.

The composition preferably comprises bulking agents 20-70 w-%, preferably 40 to 60 w-%, most preferably about 50 w-%

According to one preferred embodiment of the invention the composition comprises matrix granules not dissolving in stomach. The composition may comprise for example:

| | |
|---|---|
| Asetaldehyde binding compound(s) | 5 to 40 w-% (preferably 25 w-%) |
| Polymer not dissolving in stomach | 10 to 50 w-% (preferably 20 to 30 w-%) |
| Inert bulking agent | 20 to 70 w-% (preferably 40 to 60 w-%) |
| Ethanol | q.s. |

The polymer not dissolving in stomach may be any in pharmaceutical industry commonly used additive, such as metacrylate polymer, for example poly(ethyl acrylate-co-methyl methacrylate-co-trimethylammonioethyl methacrylate chloride 1:2:0.1) Eudragit RS or S(EUDRAGIT RS) or poly (methacrylic acid-co-methyl methacrylate 1:2) (EUDRAGIT S), or ethyl cellulose (EC). The inert bulking agent may be for example dicalcium hydrogen phosphate, microcrystalline cellulose (MCC), or other corresponding non-swelling agent. The solid substances are mixed and moistured by ethanol. The moisture mixture is granulated by using in pharmaceutical industry well known methods and devices. The dried granules can be used as such or distributed into dosages, for example into capsules.

According to another preferred embodiment of the invention the composition comprises matrix tablets not dissolving in stomach. The composition may comprise for example:

| | |
|---|---|
| Asetaldehyde binding compound(s) | 5 to 40 w-% (preferably 25 w-%) |
| Polymer not dissolving in stomach | 10 to 50 w-% (preferably 20 to 30 w-%) |
| Inert bulking agent | 20 to 70 w-% (preferably 20 to 50 w-%) |

The polymer not dissolving in stomach may be any in pharmaceutical industry commonly used additive, such as metacrylate polymer, for example Eudragit RS or S, or ethyl cellulose (EC). The inert bulking agent may be for example dicalcium hydrogen phosphate, microcrystalline cellulose (MCC), or other corresponding non-swelling agent. The solid substances are mixed and the mixture is granulated by using for example ethanol or hydrophilic polymer solution. The granules are pressed to tablets by in pharmaceutical industry well known methods and devices. The release of the effective compound(s) is now based on the diffusion of the water-soluble effective compound(s) from the pores formed to the tablet matrix.

According to one preferred embodiment of the invention the composition are protected in a form so that the compounds are not released in mouth. The granules, tablets and capsules may be covered by a water-soluble film, which effectively covers or masks the taste of acetaldehyde-binding compound(s).

According to another preferred embodiment of the invention the composition comprises substances selected from the group comprising one or more acetaldehyde-binding compound(s), water-soluble bulking agent(s) and porous film forming agent(s) for coating the preparation.

The composition preferably comprises acetaldehyde-binding compound(s) 1 to 50 w-%, preferably 5 to 40 w-%, more preferably 20 to 50 w-%, still more preferably 20 to 30 w-%. Typically the amount is about 20 to 25 w-%.

The composition preferably comprises bulking agent(s) 10-80 w-% preferably 40 to 80 w-%, more preferably 50 to 60 w-%.

The composition preferably comprises porous film forming agents, such as ethyl cellulose and hydroxypropyl methylcellulose. The relative amount of EC to HPMC may be 3/2 to 7/3.

Preparation, preferably tablets, covered by a film not dissolving in stomach. The composition may comprise for example:

| | |
|---|---|
| Asetaldehyde binding compound(s) | 1 to 50 w-% (preferably 20 to 50 w-%) |
| Water-soluble bulking agent(s) | 50 to 80 w-% (preferably 30 to 60 w-%) |
| Porous film forming agent(s) | q.s. |

The water-soluble bulking agent may be for example lactose or some other in pharmaceutical industry commonly used water-soluble bulking agent. The solid substances are mixed and the mixture is pressed to tablets by in pharmaceutical industry well-known methods and devices. The porous film may be prepared from a water-soluble polymer, such as hydroxypropyl methyl cellulose (HPMC) and water-insoluble polymer, such as ethyl cellulose (EC). The relative amount of the film forming substances, for example EC and HPMC, may be 2-5 parts EC and 1-2 parts HPMC. In the conditions of the stomach the water-soluble polymer dissolves and pores are formed to the water insoluble polymer. The release of the effective compound(s) is now based on the diffusion of the water-soluble effective compound(s) from the pores formed to the film. The film forming substances effectively mask also the taste of acetaldehyde binding compound(s).

Since acetaldehyde is formed also in the large intestine, for example in connection of drinking alcoholic beverages, it is of advantage, if the composition is protected in a form so that the compounds are not released until in the large intestine. Such a protection may be a polymer film that dissolves in an environment with a pH of 6.5 or higher, typically at pH 6.0-7.5, preferably 6.5-7.0.

A film coating, which does not dissolve in the acidic environment of the stomach, but dissolves at a pH value of 7.5 at the latest, can be made both on the tablet or the granules or the capsules. In making the preparation, it is also possible to use polysaccharides that degrade under the effect of microbes of the large intestine, or polymers generated by azo bonds. The form of preparation known by the trade name Oros™ can also be used, when its opening is first covered with an enteric polymer, the solution pH of which is ≈7.

Useful enteric polymers include, for example, the grades of hydroxypropyl methylcellulose phthalate, hydroxypropyl methylcellulose succinate or hydroxypropyl methylcellulose-acetatesuccinate (HPMC-AS) or the like, such as sold by the trade name AQOAT, AQOAT AS-HF in particular, a cellulose acetatephtalate (CAP) grade sold by the trade name AQUATERIC, and methacrylic acid derivative, methacrylic acid-methylmethacrylate copolymers, the grade sold by the trade name EUDRAGIT S (poly(methacrylic acid-co-methyl methacrylate) 1:2) in particular.

The composition according to the invention may have at least one ingredient, which adjusts the release of the effective substance not to take place until at the end of the small intestine or in the large intestine. This component can be a polymer that dissolves depending on the pH (=enteric polymer) or a polymer that degrades under the effect of the enzymes secreted by the bacteria of the large intestine. The polymer that controls the place of release can form a film around the entire preparation. It can also form a film around the particles (granules) contained by the multiple-part preparation. The polymer that degrades under the effect of the enzymes secreted by the bacteria of the large intestine can also be as a filler in a monolithic preparation, or as a filler in the granules or in a multiple-unit preparation prepared from these granules. See also WO 02/36098.

The preparation one embodiment of the invention the preparation may be an enteric tablet, the film coating of which does not dissolve until at the end of the small intestine or at the beginning of the large intestine. The dissolution pH of the polymer that forms the film may be 6.0-7.5, preferably 6.5-7.0. The amount of enteric polymer that forms the film may be 5-20%, preferably 10-15% of the whole mass of the tablet. The filler of the tablet can comprise pharmaceutical additives that do not swell, such as calcium hydrogen phosphate.

The preparation according to the invention can also be granules that comprise an acetaldehyde-binding compound(s) and are coated with an enteric film, the dissolution pH of the film-forming polymer being 6.0-7.5, preferably 6.5-7.0. The amount of film-forming enteric polymer of the entire mass of the granule may be 5-30%, preferably 15-25%. The granule can comprise 20-40%, preferably about 30% of filler poorly soluble in water, such as calcium hydrogen phosphate.

The binder of the granule coated with the enteric film, according to the invention, can be an enteric polymer, the dissolution pH of which is 6.0-7.5, preferably 6.5-7.0. The amount of binder in the granule may be 2-5%, preferably 3-4%.

The preparation according to the invention can also be a tablet comprising the enteric coated granules described above, on which an enteric film has also been made. The tablet made for such a preparation not only comprises enteric granules, but also a filler suitable for direct compression, such as microcrystalline cellulose, the amount of which in the tablet is 30-70%, preferably 40-60%.

The composition of the enteric tablet, which comprises enteric granules and binds acetaldehyde in the desired way, can be as follows, for example:

1. Enteric Granules:

| | |
|---|---:|
| Acetaldehyde-binding substance | 100 mg |
| Filler, e.g., calcium hydrogen phosphate | 30-50 mg |
| Enteric polymers | 40-60 mg |
| Enteric tablet: Enteric granules | 170-210 mg |
| Microcrystalline cellulose | 170-210 mg |
| Lubricants (e.g. magnesium stearate and talcum) | 5-10 mg |
| Enteric polymers | 30-50 mg |

Since acetaldehyde is formed also in the small intestine, for example in connection of drinking alcoholic beverages or is carried there from the stomach, it is of advantage, if the composition is protected in a form so that the compounds are not released until in the small intestine. Such a protection may be a polymer, such as poly(methacrylic acid-co-methyl methacrylate) (EUDRAGIT L 1:1), that dissolves in an environment with a pH of pH 5 to 6.

The composition of the present invention can also be in a form of a preparation comprising a fraction for binding acetaldehyde present in the stomach and in addition a fraction protected in a form so that the compounds are not released until in the large intestine. The ratio of the composition for stomach and the composition for the large intestine may be 1:1 to 1:3, typically 1:2.

The composition of the present invention can also be in a form of a preparation comprising a fraction for binding acetaldehyde present in the stomach and in addition a fraction protected in a form so that the compounds are not released until in the small intestine and in addition a fraction protected not released until in the large intestine. The ratio of the composition for stomach and the composition for the small intestine and for the large intestine may 2:1:1 to 1:3:3, typically it may be 2:1:1, 1:1:1, 1:1:2, 1:1:3, 1:2:2, 1:2:3, 1:1:3 or 1:3:3.

The preparation may comprise the substances intended for a preparation for binding acetaldehyde in the stomach. Optionally the preparation may be in the form of a capsule, such as HPMC capsule or gelatine, particularly hard gelatine.

According to another embodiment of the invention the carrier may form a gel in the stomach that floats in the contents of the stomach.

According to one further embodiment of the invention the preparation may be a liquid preparation taken orally (mixture), the physical structure of which is a gel.

According to one further embodiment of the invention the preparation may attach to the mucous membrane of the stomach.

For these embodiments the carrier may be selected from the group comprising various chitosans, alginates, such as sodium alginate, aluminium hydroxide, sodium hydrogen carbonate, sodium carboxymethyl cellulose, and sodium hydrogen carbonate as described in WO 02/36098.

The composition may be monolithic or multiparticular tablet or capsule or granule as such, which, when wetted under the influence of the gastric juices adhere to the mucous membrane of the stomach or form a gel that floats in the contents of the stomach, as a consequence of which their residence time in the stomach is prolonged and thus enables a prolonged release in and a local effect of the drug on the stomach. The long-acting preparation that locally acts on the stomach can be a liquid preparation taken orally (mixture), the physical structure of which is a gel.

A special property required of the pharmaceutical composition that has a local effect on the stomach is that it remains in the stomach for as long time as possible. Technically, this can be solved in two ways: by making a preparation that adheres to the mucous membrane of the stomach or making a preparation that floats in the contents of the stomach. The preparation can be rendered fixable to the mucous membrane of the stomach by using as additives cationic polymers, such as various chitosan grades. Preparations that float in the stomach are provided by using polymers, such as alginic acid, that form a gel and by adding to the preparation sodium hydrogen carbonate, which under the influence of gastric acid releases carbon dioxide, which in turn forms gas bubbles inside the gel. A liquid gel that floats in the stomach can also be prepared from sodium alginate, aluminium hydroxide, sodium hydrogen carbonate, and water, to which the acetaldehyde-binding compound can be added. A corresponding liquid preparation is also obtained by adding an acetaldehyde-binding substance to an aqueous dispersion of chitosan. Another preparation that remains in the stomach for a long time is a preparation, which is known as HBS™ (hydrodynamically balanced system). The preparation can remain in the stomach for a long time, when a relatively large tablet is made of it (with a diameter of at least 7-10 mm) and it is coated with a film, which does not decompose in the alimentary tract, and which, however, releases an effective substance (Oros™) through a hole which has been made to it, for example. Preferably such a preparation is consumed before, during or after eating.

When needed, the dosage may be renewed at 4 to 10-hour intervals, preferably at 6 to 8-hour intervals.

The amount of compound released in the conditions of the stomach is preferably 40-80 mg in an hour.

The preparation according to the invention, which releases in the stomach, has at least one—often two—polymers, which have the task of keeping the drug as long time as possible, for two hours minimum, in the stomach either so that it attaches the preparation to the mucous membrane of the stomach or forms a gel that floats in the contents of the stomach. Another task of the polymers is to prolong the release of the effective substance.

The preparation that locally binds acetaldehyde in the stomach can be a tablet that forms a gel in the stomach or a capsule comprising a mixture of powder or granules that forms a gel. In addition to the acetaldehyde-binding substances, the preparation comprises polymers that form a gel in the stomach, such as chitosans, alginates, sodium carboxymethylcellulose grades, carbomers or aluminium hydroxide. To advance floating in the stomach, the preparation can also comprise sodium hydrogen carbonate.

The amount of polymers in the preparation may be 10-50%, preferably 15-40%, and most preferably 20-30%.

The amount of sodium hydrogen carbonate may be 10-30%, preferably 20% of the amount of polymers.

The preparation that locally binds acetaldehyde in the stomach can be a tablet or granule preparation, wherein the acetaldehyde-binding substance is mixed with the fillers needed and, after that, granulated by using enteric polymers as binders. The binder used can be any known enteric polymer, preferably a polymer with a solution pH of 6-7, and most preferably the polymer is any of the methacrylate derivatives, which are known by the trade names EUDRAGIT L (poly(methacrylic acid-co-methyl methacrylate) 1:1) and EUDRAGIT S (poly(methacrylic acid-co-methyl methacrylate) 1:2). The amount of enteric polymer in the preparation is preferably 2-5%, most preferably 3-4%.

The preparation that locally binds acetaldehyde in the stomach can be a liquid preparation, i.e., a mixture comprising, in addition to the acetaldehyde-binding substance, also sodium alginate, aluminium hydroxide, sodium hydrogen carbonate, and water. The amount of water in the whole preparation is 70-90%, most preferably about 75-85%. The amount of sodium alginate in the preparation is preferably 2-10%, most preferably about 5%, and the amount of aluminium hydroxide is preferably 5-15%, most preferably about 10%.

The relative composition of the preparation comprising granules can be as follows, for example:

| Acetaldehyde-binding substances | 60 parts |
| Chitosan | 10-40 parts |
| Calcium hydrogen phosphate | 0-30 parts |

The relative composition of the liquid preparation can be as follows, for example:

| Acetaldehyde-binding substances | 10 parts |
| Sodium alginate | 2-10 parts |
| Aluminium hydroxide | 5-15 parts |
| Sodium hydrogen carbonate | 1-2 parts |
| Water | 70-80 parts |

An "acetaldehyde-binding compound(s)" refers to a compound(s) containing one or more free sulfhydryl and/or amino groups, preferably one or more sulfhydryl and amino group(s), most preferably in close proximity to each other (1,2- or 1,3 disubstituted aminothiols). Instead of sulfhydryl group may be used culphone group. "Compound" may be used to refer to one or more compounds. Also compounds comprising one or more SH-group(s) one or more amino group(s) function in suitable concentrations.

The "binding of acetaldehyde" preferably refers to a chemical reaction between the acetaldehyde and the compound that has a free sulphhydryl and/or amino group (instead of sulphhydryl group may be used sulphone group), wherein the acetaldehyde jointly with the "acetaldehyde-binding substance" forms a larger molecule and water can be formed in the reaction. For example, when reacting with cysteine, the acetaldehyde binds itself both to the sulphhydryl and the amino group and forms 2-methyl-L-thiazolidine-4-carboxylic acid and water. The acetaldehyde can bind itself to the amino group of almost any protein, whereby Schiff's base or a 2-methyl-imidazole ring is formed.

According to the invention, the compounds obtained from acetaldehyde by chemically binding are safe for the organism.

Suitable compounds for binding acetaldehyde in the organism also include the compounds according to the formula (I):

(I)

wherein
$R^1$ is hydrogen or an acyl group with 1-4 carbon atoms;
$R^2$ is a sulphhydryl or sulphone group;
n is 1, 2, 3 or 4.

The scope of the invention also includes the salts of the compounds of Formula I, specifically pharmaceutically acceptable salts, in particular water-soluble salts.

The scope of the invention also includes derivatives of the compounds of Formula I, specifically pharmaceutically acceptable derivatives, in particular water-soluble derivatives, capable of binding acetaldehyde in the similar manner as cysteine.

The substances according to the following formula are capable of binding acetaldehyde:

$$R-NH_2 \quad (II)$$

wherein R is derived from a protein (e.g., haemoglobin, albumin or tubuline)

In a reaction of the compound according to the formula (II) with acetaldehyde, a Shiff's base according to the formula (III) is formed, $$R-N=CHCH_3 \quad (III)$$

wherein
R is derived from a protein (e.g., haemoglobin, albumin or tubuline).

Amino acids or other compounds or the salts thereof that suitably bind acetaldehyde and contain a free sulphhydryl and/or amino group (instead of suphhydryl group may be used sulphone group) include, for example:
L-cysteine,
D-cysteine,
cystine,
cysteic acid,
cysteine glycine,
threo or erythro-β-phenyl-DL-cysteine,
β-tetramethylene-DL-cysteine,
methionine,
serine,
D-penicillamine or its dipeptides with N-terminals,
peptide or a protein with terminal cysteine
semicarbazide,
glutathione,
reduced glutathione,
β-mercaptoethylamine,
D, L-homocysteine,
D,L-homocysteic acid,
N-acetylcysteine,
L-cysteinyl-L-valine,
β-β-tetramethylene-DL-cysteine,
cysteinyl-glycine,
mercaptoethylglycine,
tre-(5)-β-phenyl-DL-cysteine,
erythro-β-phenyl-DL-cysteine,
cysteine hydrochloride,
thiaminhydrochloride,
sodiummetabisulphite,
arginine,
glycine,
lycine,
ammonium chloride,
1,4-dithiothreitol,
mercaptanes.

It is of advantage to add to the compositions of the present invention at least one of the substances selected from the group comprising chromium, vitamin B12, A-, D-, E, -C-vitamins, niacin, biotin, thiamine, B2-, B5-, B6-vitamins and folic acid and trace elements, such as chromium, manganese, selenium, zink and iron.

However, only those acetaldehyde-binding compounds, which are non-toxic and suitable for human consumption, can be applied to the compositions according to the present invention. These compounds should not cause a health hazard in the amounts used.

Cysteine and its derivatives are especially well suited to the purpose according to the invention. The most suitable amino acids for the use according to the invention comprise L- and D-cysteines, compounds that are converted to cysteine or compounds which function in the same way as the L- or D-cysteines, the derivatives or salts of cysteine, especially water-soluble derivatives or salts, The most preferred compound(s) are in addition to L-cysteine and D-cysteine, D-penicillamine, β-mercaptoethylamine and N-acetylcysteine, a compound converted to cysteine, or a salt or a structural analogue of these compounds capable of binding acetaldehyde. The most preferred compound is L-cysteine and the salts thereof.

Useful compound to be added to the composition of the invention and for binding acetaldehyde is also lecithin.

A "harmful/carcinogenic content of acetaldehyde" in the human mouth, oesophagus, stomach, small intestine and large intestine is 20 to 800 μmol/l of saliva or the contents of the intestine, a content of as low as about 20 to 50 μM causing carcinogenic mutations on the cell level. Hence, it would be advisable to aim at a zero concentration of acetaldehyde in these areas.

Keeping the acetaldehyde content essentially lower than without the use of the composition means that the acetaldehyde content should be kept at a level that is at least 20%, preferably over 40%, and most preferably over 60% lower than when not using the composition according to the description of the invention.

Such a harmful or carcinogenic content of acetaldehyde in the human mouth, oesophagus, stomach or small intestine or large intestine can be obtained in connection with consuming alcoholic drinks, particularly strong alcoholic drinks, or foodstuffs containing alcohol, as a consequence of smoking, when consuming products containing acetaldehyde and in particular in people having atrophic gastritis or achlorhydric stomach.

"Alcoholic drinks" are ethanol-containing drinks, their ethanol content varying within 0.7% by volume and 84% by volume."

"Alcoholic foodstuffs" refer to foodstuffs containing at least 0.7% of ethanol. Such foodstuffs can be, for example, fermented juices or preserves, or foodstuffs preserved with small amounts of alcohol, pastries, jellies, and mousse seasoned with liqueur or corresponding products containing alcohol.

"Acetaldehyde comprising foodstuffs" refers to foodstuffs containing acetaldehyde. Acetaldehyde is contained in foodstuffs, which have ethanol that is generated in connection with fermentation, such as beer, cider, wine, home-brewed beer, and other alcoholic drinks, as well as many juices. In certain foodstuffs, such as some milk products, acetaldehyde is used for preservation purposes and to add flavour, or the acetaldehyde is formed in the product as a consequence of microbial activity. For example, sugary juices or sugar-containing foodstuffs, in general provide a food substrate for microbes. High concentrations of acetaldehyde are formed, for example, in fermented milk products, such as yoghurt. The microbes used to make yoghurt produce acetaldehyde in the yoghurt. As for alcoholic drinks, sherry and Calvados contain especially large amounts of acetaldehyde.

The use of the compositions according to the invention can be of benefit even, when light alcoholic drinks are enjoyed or foodstuffs are consumed, which contain small amounts of alcohol.

"In connection with consuming alcoholic drinks" herein refers to the period of time that begins from starting to enjoy alcohol and ends, when there is no more alcohol in the blood.

"In connection with smoking" herein refers to the period of time that begins from starting to smoke and ends, when smoking is stopped.

"In connection with eating" herein refers to the period of time before, during and after eating.

According to one preferred embodiment of the invention the composition of the present invention is administered to people having an increased risk of developing cancer in the stomach. The acetaldehyde present on these areas can be locally bound by using the composition according to the invention into a harmless form by consuming the said compositions during or after eating.

According to a preferred embodiment of the invention the composition of the present invention is added to a food composition just before eating. The food composition may be a foodstuff packed into a first package and the composition comprising the acetaldehyde-binding compounds containing composition may be packaged to a second package. The second package may comprise also a foodstuff(s).

The first food composition may, for example, be selected from the group comprising milk, milk products, milk desserts, milk dishes, milk sauces, sour milk, soured whole milk, cheese, ice-cream and yoghurt. If the second food composition comprises a foodstuff, it may be some dry foodstuff, such as grain products, in particular cereal products, for example muesli and cereals.

According to one preferred embodiment of the invention the composition of the present invention is administered to people having atrophic gastritis or achlorhydric stomach.

In particular, the composition of the present invention is administered to people having a value outside the reference range or cut-off values of at least one of the biomarkers of atrophic gastritis selected from the group comprising pepsinogen I, pepsinogen II, pepsinogen I/pepsinogen II ratio and gastrin-17 B (fast) and gastrin-17S (stimulated). Also high HPAB (*Helicobacter pylori* antibody) value indicates a risk for developing atrophic gastritis. A suitable method and kit for examining the biomarkers is the commercially available GastroPanel® examination and software supporting its use (www.biohit.com/gastropanel, www.biohit.com/gastrosoft). The screening for atrophy of the corpus, mucosa of the whole stomach and antrum is described in U.S. Pat. No. 6,696,262.

EXAMPLES

Example 1

Gel Forming Formulation for Prolonged Binding of Acetaldehyde in the Stomach

The locally long-acting preparation that binds acetaldehyde in the stomach can be prepared and used to decrease the risk of cancer caused by acetaldehyde as follows:

The relative composition of the preparation that locally binds acetaldehyde in the stomach can be as follows, for example:

| | |
|---|---|
| Cysteine | 60 parts |
| Chitosan | 10-40 parts |
| Calcium hydrogen phosphate | 0-30 parts |

The powder mixture is mixed by conventional mixers (such as a blender), which are used in the pharmaceutical industry. After that, the powder mixture is granulated using a 2.5% acetic acid as a granulation liquid. The granulation liquid can be added to the same blender. The moist powder mass is pressed through a screen plate or a perforated plate (the diameter of the aperture being 2 mm). The formed granules are dried and screened. A screen fraction of 1.2-1.7 mm is recovered, which is dispensed into hard gelatine capsules so that the dose of cysteine is 100 mg. In the stomach gastric juice wet cysteine/chitosan granules forming a hydrogel. Gel starts to release cysteine in a prolonged way and reacts with acetaldehyde. Chitosan as gel forming component can be replaced by other well known gel forming pharmaceutical additives (e.g. alginic acid).

Example 2

Non-Disintegrating Matrix Tablet for Binding Acetaldehyde in the Stomach

The relative composition can be as follows:

| | |
|---|---|
| Cysteine | 25 parts |
| EUDRAGIT RS (poly(ethyl acrylate-co-methyl methacrylate-co-trimethyl-ammonioethyl methacrylate chloride 1:2:0.1) | 20-30 parts |
| Microcrystalline cellulose | 20-50 parts |

From the powder mixture tablets containing 100-200 mg of cysteine can be compressed with equipments generally used in pharmaceutical industry. The tablet is a monolitic matrix tablet which does not disintegrate in the stomach. The active compound will release and dissolve in gastric fluid in a prolonged way leading to sustained acetaldehyde binding effect. EUDRAGIT RS (poly(ethyl acrylate-co-methyl methacrylate-co-trimethylammonioethyl methacrylate chloride) 1:2:0.1) as a water insoluble binder can be replaced with similar pharmaceutical additives (e.g. ethylcellulose)

Example 3

Film Coated Tablets for Binding Acetaldehyde in the Stomach

Pharmaceutical formulations releasing acetaldehyde-binding compound(s) in a sustained manner in the stomach can also be developed based on tablets coated with a porous film. The composition of the tablet core can be:

| | |
|---|---|
| Cysteine (20-50 parts) | 30 parts |
| Lactose | 50-80 parts |
| Magnesium stearate | 1-2 parts |
| Talcum | 1-2 parts |

From the powder mixture tablets are compressed and film-coated utilizing techniques commonly used in pharmaceutical industry. The content of the coating solution can be, e.g.

| | |
|---|---|
| Ethyl cellulose | 2-5 parts |
| Hydroxypropyl methylcellulose (HPMC) | 1-2 parts |
| Ethanol | 95 parts |

In the gastro-intestinal tract ethyl cellulose does not dissolve but HPMC dissolves forming pores to the film allowing cysteine to release from the tablet in a sustained manner.

Example 4

Non-Disintegrating Granules for Sustained Release of Acetaldehyde-Binding Substances in the Stomach The relative compositions can be as follows, for example:

| | |
|---|---|
| Cysteine | 25 parts |
| EUDRAGIT RS (poly(ethyl acrylate-co-methyl methacrylate-co-trimethyl-ammonioethyl methacrylate chloride) 1:2:0.1) or ethylcellulose | 20-30 parts |
| Microcrystalline cellulose | 40-60 parts |
| Ethanol | q.s. |

Powdery substances are mixed and moistened by ethanol in equipments commonly used in pharmaceutical industry. The moistened mixture is granulated and dried by well-known methods. If required, the matrix granules formed can be coated with a low molecular weight hydroxypropyl methylcellulose film in order mask the taste of cysteine. Sufficient amounts of granules containing a single dose (100-200 mg) of cysteine can be dispensed into gelatine capsules or compressed with microcrystalline cellulose, e.g. to tablets.

Example 5

Combination Product for Binding Acetaldehyde in the Stomach, Intestine and Colon In practice it is quite often important to bind acetaldehyde in the stomach, intestine and colon at the same time. If a person suffers from achlorhydric or low acid stomach he or she most likely has acetaldehyde in the stomach. At the same time it is most likely that acetaldehyde can be found also in the intestine. If the person consumes alcoholic beverages it is obvious that acetaldehyde can be found also in the colon. For these reasons it is of advantage to develop a single formulation, which can release acetaldehyde-binding compound(s) and bind acetaldehyde in the whole length of the gastro-intestinal tract. For that purpose three different subformulations are incorporated to the same pharmaceutical product.

| | | |
|---|---|---|
| Fraction 1 | Equal to Example 4 | Release in the stomach |
| Fraction 2 | Consisting of Example 4 plus a film coat dissolving at pH 5-6 | Release in the intestine |
| Fraction 3 | Consisting of Example 4 plus a film coat dissolving at pH 6.5-7.5 | Release in the colon |

The relative amounts of fractions 1, 2 and 3 can be 2:1:1, 1:1:1, 1:1:2, 1:2:2, 1:2:3 or 1:1:3. Fraction 1 can be prepared as described in Example 4. Fractions 2 and 3 can be manufactured by film coating with well-known film-coating techniques. The film forming polymer for Fraction 2 could be EUDRAGIT L (poly(methacrylic acid-co-methyl methacrylate) 1:1), e.g., and for Fraction 3 EUDRAGIT S (poly(methacrylic acid-co-methyl methacrylate) 1:2), e.g. The most convenient final product could be a hard gelatine or HPMC capsule. The total amount of cysteine in the combination product could be 200 to 500 mg.

Example 6

A composition comprising acetaldehyde-binding compound(s) was prepared as described in the earlier examples.

| | |
|---|---|
| L-cysteine | 25 w-% |
| Metacrylate polymer (EUDRAGIT RS (poly(ethyl acrylate-co-methyl methacrylate-co-trimethylammonioethyl methacrylate chloride) 1:2:0.1)) | 25 w-% |
| Microcrystalline cellulose | 50 w-% |

The solid substances were mixed carefully in a suitable device. Ethanol was added in small amounts continuously mixing until a powder mixture having sufficient moisture was obtained. The moisture powder mixture was granulated by any in pharmaceutical industry commonly used method. The formed granules were dried.

The dissolution experiment was carried out by using an "artificial stomach". 25 ml of juice and yoghurt contaminated with mouth bacteria were added to 100 ml bottles, which were incubated one day at room temperature. A preparation comprising 250 mg of L-cysteine was added to the bottles and they were slowly shaken at 37° C.

It was found that within 2 hours the total amount of acetaldehyde formed from the substrate was bound into harmless form.

Example 6

A composition comprising 20-100 mg acetaldehyde-binding compound(s) is prepared as described in the earlier examples and is mixed with muesli and packed in a separate package of about 10 to 100 ml in volume. Yoghurt is packaged into a package of about 100-200 ml. The two packages are packed together and sold as connected to each other or sold together, but not connected to each other.

LITERATURE

Biemond J, Kreuning J, Jansen J B, Lamers C B. Serum pepsinogens in patients with gastric diseases or after gastric surgery. Scand J Gastroenterol 1994; 29:238-42

Brunner G, Hell M, Hengels K J, Hennig U, Fuchs W. Influence of lasoprazole on intragastric 25-hour pH, meal.-stimulated gastric acid secretion, and concentrations of gastrointestinal hormones and enzymes in serum and gastric juice in healthy volunteers. Digestion 1995; 56:137-144

Di Mario F, Franze A, Cavallaro L G. Non-Invasive Diagnosis for Gastric Diseases. One Global Medicine s.r.l. 2004; 1-48, www.biohit.com/Literature/Dignostics; 2004 Books DiMario F, Cavallaro L G, Liatopoulou A, ym. Accuracy of "serological gastric biopsy" in a cohort dyspeptic patients, Poster presentation at the DDW 2005, May 15-18, in Chigago, Ill., USA Festen H P, Thijs L C, Lamers C B, Jansen J M, Pals G, Frants R R, Defize J, Meuwissen S G. Effect of oral omeprazole on serum gastrin and serum pepsinogen I levels. Gastroenterology 1984; 87:1030-1034

Fraser A G, Lam W M, Luk Y W, Sercombe J, Sawyerr A M, Hudson M, Samloff I M, Pounder R E. Effect of ranitidine bismuth citrate on postprandial plasma gastrin and pepsinogens. Gut 1993; 34:338-342

Färkkilä M, Miten dyspepsiaa tulisi hoitaa, Duodecim 2004; 120: 2537-42

Gatta L, Perna F, Ricci C, ym. Effect of proton pump inhibitors and antacid therapy on $^{13}$C urea breath test and stool test for *Helicobacter pylori* infection. Am J Gastroenterol 2004; 99:823-829

Gillen D, Wirz A A, Ardill J E, McColl K E. Rebound hypersecretion after omeprazole and its relation to on-treatment acid suppression and *Helicobacter pylori* status. Gastroenterology 1999; 117:513-4

Graham K S, Graham D Y. Contemporary Diagnosis and Management of *H. pylori*-Associated Gastrointestinal Diseases, Published by Handbooks in Health Care Co, Newtown, Pa., USA, 2002

Graham D Y, Opekun A R, Hammoud F, Yamaoka Y, Reddy R, Osato M S, El-Zimaity H M. Studies regarding the mechanism of false negative urea breath tests with proton pump inhibitors. Am J. Gastroenterol. 2003; 98:1005-9.

Hellstrom P M, Vitols S: The choice of proton pump inhibitor: does it matter? Basic Clin Pharmacol Toxicol 94:105, 2004.

Iwao T, Toyonaga A, Kuboyama S, Tanikawa K. Effects of omeprazole and lanzoprazole on fasting and postprandial serum gastrin and serum pepsinogen A and C. Hepatogastroenterology 1995; 42:677-682

Jauhonen P. Kajaanin dyspepsiatutkimuksesta henkilokohtainen tiedonanto 2005

Järvinen L. Tapausselostus: GastroPanel—uusi ase dyspepsian turvallisen hoidon kehittämiseen, Yksityislääkäri 2005; 2: 94-98

Kokkola A, Rautelin H, Puolakkainen P, ym. Positive result in serology indicates active *Helicobacter pylori*-infection in patients with atrophic gastritis. J Clin Microbiol 1998; 36 (6):1808-10148.

Kokkola A, Rautelin H, Puolakkainen P ym. Diagnosis of *Helicobacter pylori*-infection in Patients with Atrophic Gastritis: Comparison of Histology, $^{13}$C Urea Breath Test, and serology. Scand J Gastroenterol 2000; 25:138-141

Lamers C B, Rotter J I, Fansen J B, Samloff I M. Serum pepsinogen I in familial multiple endocrine neoplasia type I. Dig Dis Sci 1988; 33:1274-6

Lazzaroni M, Sangaletti O, Bianchi Porro G. Gastric acid secretion and plasma gastrin during short-term treatment with omeprazole and ranitidine in duodenal ulcer patients. Hepatogastroenterology 1992; 39:366-370

Ohsawa T, Hirata W, Higichi S. Effects of three H2-receptor antagonists (cimetidine, famotidine, ranitidine) on serum gastrin level. Int J Clin Pharmacol Res 2002; 22:29-35

Sandeleanu S, Strindsberg M, Jonkers D, Hameeteman W, Biemond I, Lundqvist G, Lamers C, Stockbrugger R W. Serum gastrin and chromogranin A during medium- and long-term acid suppressive therapy: a case-control study. Aliment Pharmacol Ther 1999; 13:145-153

Schumann K M, Massarrat S. Changes in total pepsin activity and pepsinogen I in human sera under stimulation and inhibition of gastric acid secretion. Hepatogastroenterology 1991; 38 Suppl 1:33-36

Stoschus B, Hamscher G, Ikonomou S, Partoulas G, Eberle C, Sauerbruch T, Feurle G E. Effect of omeprazole treatment on plasma concentrations of the gastric peptides, xenin, gastrin and somatostatin, and of pepsinogen. J Pept Res 1998; 52:27-33

Manes G, Menchise A, deNucci C. Empirical prescribing for dyspepsia: a randomised controlled trial of test and treat versus omeprazole treatment. BMJ 2003; 326:1118-1123

Modlin I M, Kidd M, Marks I N, Tang L H. The pivotal role of John S. Edkins in the discovery of gastrin. World J Surg 1997; 21:226-234

Nurgalieva Z, El-Zimaity H, Graham D, ym. Gastric atrophyt in North America: Histology vs. Non-invasive testing, Poster presentation at the DDW 2005, May 15-18, in Chigago, Ill., USA Pasechnikov V D, Chukov S Z, Kotelevets S M, ym. Invasive and non-invasive diagnosis of *Helicobacter pylori*-associated atrophic gastritis: A comparative study, Scand J Gastroenterol 2005; 40: 297-301

Qvigstad G, Waldum H. Rebound hypersecretion after inhibition of gastric acid secretion. Basic Clin Pharmacol Toxicol 2004; 94:202-8

Puustinen R. Helsingin kaupungin terveysasemien lääkäreiden käytettävissä olevia, "Käypä hoito"-suosituksen pikavalikoilta saatavia "gastroenterologisia tutkimuksia", henkilökohtainen tiedonanto 2005

Rugge M, Correa P, Dixon M F. ym. Gastric mucosal atroohy: interobserver consistency using new criteria for classification and grading. Aliment Pharmacol Ther 2002; 16:1-12

Sachs G, Prinz C, Loo D, etc: Gastric acid secretion: activation and inhibition. Yale J Biol Med 67:81-95, 1994.

Salaspuro M. Ovatko "testaa ja hoida"-strategian haitat hyötyä suuremmat, Duodecim 2005; 8:852-853

Salaspuro M. Dyspepsian kaksiportaisen seulontamenetelman markkinointi on ennenaikaista, Duodecim 2005; 121:1191-3.

Salaspuro, V., Hietala, J., Kaihovaara, P., Pihlajarinne, L., Marvola, M. & Salaspuro, M.: Removal of acetaldehyde from saliva by a slow-release buccal tablet of l-cysteine. Int. J. Cancer 97: 361-264, 2002.

Salaspuro, V., Hietala, J., Marvola, M. & Salaspuro, M.: Eliminating carcionogenic acetaldehyde by cysteine from saliva during smoking Cancer Epidem. Biomark. Prev. 15: 146-149, 2006.

Samuelson L C, Hinkle K L: Insights into the regulation of gastric acid secretion through analysis of genetically engineered mice. Annu Rev Physiol 65:383-400, 2003.

Schubert M L. Gastric secretion. Curr Opin Gastroenterol 2004; 20:519-25

Shamburek R D, Schubert M L: Control of gastric acid secretion. Histamine H2-receptor antagonists and H+K(+)-ATPase inhibitors. Gastroenterology Clinics of North America. 21:527-550, 1992.

Sipponen P, Härkönen M, Alanko A. Atrofisen gastriitin toteaminen verinäytteestä. Suomen Lääkärilehti 2001; 38: 3833-3839

Sipponen P, Ranta P, Helske T, ym. Serum Levels of Amidated Gastrin-17 and Pepsino gen I in Atrophic Gastritis: An Observation Case-Control Study, Scand J Gastroenterol 2002 (7): 785-

Sipponen P, Laxen F, Huotari K, ym. Prevalence of Low Vitamin B12 and High Homocysteine in Serum in an Elderly Male Population: Association with Atrophic Gastritis and *Helicobacter pylori* infection, Scand J Gastroenterol 2003; 12: 1209-

Sipponen P, Vauhkonen M, Helske T, ym. Patients with Barrett's esophagus show low circulating levels of gastrin-17, World Gastroenterol 2005, in press Talley N J, Vakil N, Delaney G, ym. Management issues in dyspepsia: current consensus and controversies. Scand J Gastroenterol 2004; 39 (10): 913-918

Uemura N, Okamoto S, Yamamoto S, ym. *Helicobacter pylori* infection and the development of gastrici cancer, N Eng J Med 2001; 345:784-789

Varis K, Sipponen P, Laxen F ym. the Helsinki Gastritis Study Group, Implications of serum pepsinogen I in early endoscopic diagnosis of gastric cancer and dysplasia, Scand J Gastroenterol 2000; 9: 950-956.

Väkeväinen, S., Mentula, S., Nuutinen, H., Salmela, K., Jousimies-Somer, H., Färkkilä, M. & Salaspuro, M. et al.: Ethanol-derived microbial production of carcinogenic acetaldehyde in achlorhydric atrofic gastritis. Scand. J. Gastroeterol 37: 648-655, 2002.

Väkeväinen, S., Tillonen, J., Salaspuro, M., Jousimies-Somer, H., Nuutinen, H., Färkkilä. M.: Hypochlorhydria induced by a proton pump inhibitor leads to intragastric microbial production of acetaldehyde from ethanol. Aliment. Pharmacol. Ther. 14: 1511-1518, 2000.

Väänänen H, Vauhkonen M, Helske T, ym. Non-Endoscopic Diagnosis of Atrophic Gastritis with a Blood Test. Correlation between Gastric Histology and Serum Levels of Gastrin-17 and Pepsinogen I. A Multicenter Study. Eur J Gastroenterol Hepatol 2003; 15: 885-891

Waldum H L, Brenna E, Sandvik A K. Long-term safety of proton pump inhibitors: risks of gastric neoplasia and infections. Expert Opin Drug Saf 2002; 1:29-38

Welage L S: Pharmacologic properties of proton pump inhibitors. Pharmacotherapy 23:74 S-80S, 2003.

Whiting J L, Sigurdsson A, Rowlands D C, ym. The long term results of endoscopic surveillance of premalignant lesions. Gut 2002; 50:378-81.

Wyeth Uutiset lääkäreille. Kaksiportainen menetelmä seuloo dyspepsiaa sairarastavat. Wyeth 2005; 4.

Zagari R M, Nicolini G, Casanova S, ym. Diagnosis of atrophic gastritis in the general population based upon a combination of three non invasive tests, Gut 2002; 51 (suppl 11): A39.

Yao X, Forte J G: Cell biology of acid secretion by the parietal cell Annu Rev Physiol 65:103-131, 2003.

The invention claimed is:

1. A non-toxic composition in the form of a monolithic or multiparticular preparation which binds acetaldehyde present in a whole length of the gastrointestinal tract, wherein said composition comprises one or more acetaldehyde-binding compound(s), comprising one or more free sulphhydryl and/or amino groups, wherein said compound(s) are mixed with a non-toxic carrier that effects sustained release of said compound(s) in the gastrointestinal tract, wherein the non-toxic carrier is selected from polymers that do not disintegrate in the stomach, polymers that form a gel which floats in the contents of the stomach and polymers that attach to the mucous membrane of the stomach, wherein subunits of the composition are coated with a polymer film that dissolves in an environment of a pH of 6.5 or higher, and wherein the composition comprises a fraction for binding acetaldehyde present in the stomach, a fraction of the composition protected in a form so that the compounds are not released until in the intestine, and a fraction of the composition protected in a form so that the compounds are not released until in the colon, and the relative amount of fractions for the stomach, the intestine and for the colon are selected from the group consisting of 2:1:1, 1:1:1, 1:1:2, 1:2:2, 1:2:3 and 1:1:3.

2. The composition according to claim 1, wherein the composition comprises substances selected from the group comprising one or more acetaldehyde-binding compound(s), a polymer(s) not disintegrating in the stomach and a bulking agent(s).

3. The composition according to claim 2, wherein the amount of acetaldehyde-binding compound(s) is 1 to 40 wt %, the amount of polymer(s) not disintegrating in the stomach in the composition is 10-50 wt % and the amount of bulking agent(s) in the composition is 20-70 wt %.

4. The composition according to claim 2, wherein the polymer not dissolving in the stomach is a methacrylate polymer.

5. The composition according to claim 4, wherein the polymer not dissolving in the stomach forms a matrix, allowing said acetaldehyde-binding compound(s) to diffuse in a sustained manner into the stomach.

6. The composition according to claim 5, wherein the composition is in the form of a matrix tablet or matrix granule.

7. The composition according to claim 1, wherein the composition is coated with a water-soluble film.

8. The composition according to claim 1, wherein the composition comprises substances selected from the group comprising one or more acetaldehyde-binding compound(s), a water-soluble bulking agent(s) and at least two film forming agents coating the composition by a film.

9. The composition according to claim 1, wherein the amount of acetaldehyde-binding compound(s) is 1 to 50 wt % and the amount of a water-soluble bulking agent(s) is 50 to 80 wt %.

10. The composition according to claim 8 or 9, wherein the first of said film forming agents is water-insoluble and the second of said film forming agents is water-soluble, said first film forming agent forming a continuous film and said second film-forming agent forming pores to the film allowing said acetaldehyde-binding compound(s) to diffuse in a sustained manner into the stomach.

11. The composition according to claim 9, wherein the water-soluble component in the film consists of hydroxypropyl methylcellulose (HPMC) and said water-insoluble component in the film consists of ethyl cellulose and/or Eudragit RS.

12. The composition according to claim 1, wherein the fractions are in the form of a tablet or capsule.

13. The composition according to claim 1, wherein the composition comprises 1-500 mg of acetaldehyde-binding substance per single dose.

14. The composition according to claim 1, wherein the composition is in the form of a tablet, a capsule, a granule or powder or a combination of these.

15. The composition according to claim 14, wherein the composition is in the form of a tablet or capsule the diameter of which is at least 7 mm.

16. The composition according to claim 1, wherein said one or more acetaldehyde-binding compound(s) comprises one or more free sulphhydryl and/or amino groups.

17. The composition according to claim 1, wherein said one or more acetaldehyde-binding compound(s) is represented by formula (I)

$$R^1-NH-CH-COOH \atop | \atop (CH_2)_n-R^2 \qquad (I)$$

wherein
$R^1$ is hydrogen or an acyl group with 1-4 carbon atoms,
$R^2$ is a sulphhydryl or sulphone group, and
n is 1, 2, 3 or 4,
or is a salt or a derivative of any of these compounds capable of binding acetaldehyde.

18. The composition according to claim 1, wherein the composition comprises one or more acetaldehyde-binding compound(s) selected from the group comprising L-cysteine, D-cysteine, cystine, cysteic acid, cysteine glycine, threo-β-phenyl-DL-cysteine, erythro-β-phenyl-DL-cysteine, β-tetramethylene-DL-cysteine, D-penicillamine and an N-terminal dipeptide of D-penicillamine, semicarbazide, glutathione, reduced glutathione, DL-homocysteine, N-acetylcysteine, L-cysteinyl-L-valine, β-β-tetramethylene-DL-cysteine, cysteinyl glycine, mercaptoethyl glycine, tre(5)-β-phenyl-DL-cysteine, erythro-β-phenyl-DL-cysteine, cysteine hydrochloride, thiamine hydrochloride, sodium metabisulphite, serine, methionine, β-mercaptoethylamine, arginine, lecithin, glycine, lycine, ammonium chloride, 1,4-dithiothreitol and mercaptanes or a salt of any of these compounds, and optionally at least one of the substances selected from the group comprising vitamin B12, A-, D-, E, -C-vitamin, niacin, biotin, thiamine, B2-, B5-, B6-vitamin, folic acid, chromium, manganese, selenium, zinc and iron.

19. The composition according to claim 1, wherein said one or more acetaldehyde-binding compound(s) is L-cysteine, D-cysteine, D-penicillamine, N-acetylcysteine, a compound converted to cysteine, a salt or a structural analogue of these compounds capable of binding acetaldehyde.

20. The composition according to claim 1, wherein the compound(s) are released in the stomach for at least 30 minutes.

21. The composition according to claim 1, wherein the compound(s) are released in the stomach for 0.5 to 8 hours.

22. A food additive, characterized in that it comprises the composition according to claim 1.

23. A food composition, characterized in that it comprises the composition according to claim 1.

24. A food package, characterized in that it comprises a first package and a second package, said first package comprising a foodstuff, and said second package comprising the composition according to claim 1.

25. The food package according to claim 24, wherein the composition according to claim 1 is mixed with a foodstuff.

26. The food package according to claim 24, wherein the foodstuff is selected from the group consisting of milk, milk products, milk desserts, milk dishes, milk sauces, sour milk, soured whole milk, cheese, ice-cream and yogurt.

27. The food package according to claim 24, wherein the foodstuff is a grain product.

28. The composition according to claim 4, wherein the methacrylate polymer is Eudragit L, S or RS, or ethyl cellulose, or a combination of these.

29. The composition according to claim 7, wherein the water-soluble film is hydroxypropylmethylcellulose (HPMC) film.

30. The composition according to claim 7, wherein the water-soluble film is inside a hard gelatine or hydroxypropylmethylcellulose (HPMC) capsule or tablet or other form of preparation.

31. The composition according to claim 1, wherein the fractions are in the form of a hard gelatine or HPMC capsule.

* * * * *